(12) United States Patent
Kamal et al.

(10) Patent No.: US 8,309,726 B2
(45) Date of Patent: Nov. 13, 2012

(54) SUBSTITUTED PIPERAZINE COMPOUNDS OF FORMULA 8

(75) Inventors: Ahmed Kamal, Hyderabad (IN); Bandari Rajendra Prasad, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 278 days.

(21) Appl. No.: 12/307,570

(22) PCT Filed: Mar. 13, 2008

(86) PCT No.: PCT/IN2008/000143
§ 371 (c)(1), (2), (4) Date: Jul. 23, 2009

(87) PCT Pub. No.: WO2008/114275
PCT Pub. Date: Sep. 25, 2008

(65) Prior Publication Data
US 2010/0016589 A1    Jan. 21, 2010

(30) Foreign Application Priority Data
Mar. 19, 2007 (IN) .............................. 594/DEL/2007

(51) Int. Cl.
*C07D 295/00* (2006.01)
(52) U.S. Cl. ...... 544/386; 544/242; 544/283; 546/268.1
(58) Field of Classification Search .................. 544/242, 544/283, 386; 546/268.1
See application file for complete search history.

(56) References Cited

FOREIGN PATENT DOCUMENTS
WO      WO 98/17648 A1    4/1998
WO      WO 2008/114275   *   9/2008

OTHER PUBLICATIONS

Jordan, V. C. Nature Reviews: Drug Discovery, 2, 2003, 205.*
Cocco et al., "Synthesis of new N-(2-(trifluoromethyl)pyridin-4-yl)anthranilic acid derivatives and their evaluation as anticancer agents", *Bioorg. Med. Chem. Lett.*, 14(23):5787-5791 (2004).
Labrie et al., "In vitro activity of novel dual action MDR anthranilamide modulators with inhibitory activity at CYP-450", *Bioorg. Med. Chem.*, 14(23):7972-7987 (2006).

* cited by examiner

*Primary Examiner* — Douglas M Willis
(74) *Attorney, Agent, or Firm* — DLA Piper LLP (US)

(57) ABSTRACT

The present invention provides novel anthranilic acid derivative useful as potential anticancer agent. More particularly, the present invention relates novel anthranilic acid derivative of general formula (8), R'=alkyl-2-methoxyphenyl piperazine or benzyl; R=2-methoxyphenyl, piperazine, 2-pyridyl piperazine-1-yl, 2-pyrimidyl piperazine-1-yl, 4-quinazolinyl piperazine-1-yl, 9H-9-fluorenylamine, 4-{(2{amino-5-(methoxy)-4-[(phenylmethyl)oxy]phenyl}carbonyl)-hexahydro-1-pyrazinyl], and [(4[2-amino-4-(benzyloxy)-5-methoxybenzoyl]aminophenyl)-sulfonyl]-4-benzamine; X=H or pyrazine-2-carbonyl. The present invention also provides a process for the preparation of novel anthranilic acid derivative of general formula (8), which is useful as potential anticancer agent.

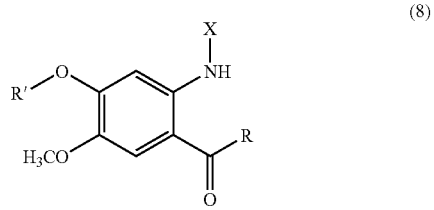

(8)

9 Claims, No Drawings

SUBSTITUTED PIPERAZINE COMPOUNDS OF FORMULA 8

CROSS REFERENCE TO RELATED APPLICATIONS

This application is a 35 USC §371 National Stage application of International Application No. PCT/IN2008/000143 filed Mar. 13, 2008, now pending; which claims the benefit under 35 USC §119(a) to India Patent Application No. 594/DEL/2007 filed Mar. 19, 2007. The disclosure of each of the prior applications is considered part of and is incorporated by reference in the disclosure of this application.

FIELD OF THE INVENTION

The present invention relates to novel anthranilic acid derivative useful as potential anticancer agent. More particularly, the present invention relates novel anthranilic acid derivative of general formula 8:

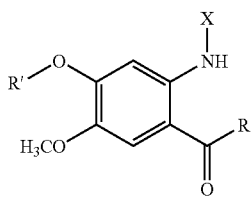

8

R'=alkyl-2-methoxyphenyl piperazine or benzyl;
R=2-methoxyphenyl piperazine, 2-pyridyl piperazine-1-yl, 2-pyrimidyl piperazine-1-yl, 4-quinazolinyl piperazine-1-yl, 9H-9-fluorenylamine, 4-[(2{amino-5-(methoxy)-4-[(phenyl-methyl)-oxy]phenyl}-carbonyl)hexahydro-1-pyrazinyl], and [(4 [2-amino-4-(benzyloxy)-5-methoxybenzoyl]aminophenyl)sulfonyl]-4-benzamine; and
X=H or pyrazine-2-carbonyl.

The present invention also relates to a process for the preparation of novel anthranilic acid derivative of general formula 8, which is useful as potential anticancer agent.

BACKGROUND OF THE INVENTION

An efficient synthesis of new anthranilic acid derivatives led us to identify a series of potential anticancer agents. The in vitro anticancer screening performed by the NCI reveals that some esters of N-(2-(trifluoromethyl)pyridin-4-yl)anthranilic acid demonstrated interesting inhibitory properties against a wide array of human tumour cell lines. In particular, compounds 8a, 8b, 8c, 8d and 8e exhibited antiproliferative activity in nanomolar to low micromolar concentrations against most of the tested cell lines. On the basis of observed biological activities and compare analysis, putative cox-dependent/independent mechanisms responsible for antitumour activity were proposed.

Among the wide variety of synthetic compounds recognized as potential anticancer drugs, molecules based on the anthranilic acid scaffold have attracted great interest in recent years. Experimental and preclinical models demonstrated that a number of these compounds elicited outstanding anticancer activity through a range of biological activities implicated with the development and maintenance of tumour cells. In this context, several reports describing the antitumbur evaluation of anthranilate derivatives appeared in the recent literature. For example, Tranilast (FIG. 1) has been reported to exhibit antiproliferative activity against cultured leiomyoma cells, through the oppression of cyclin-dependent kinase (CDK) 2 activity. Yashiro et al. have described that Tranilast decreases the production of matrix metallo-proteinase-2 (MMP-2) and transforms the growth factor-a1 (TGF-a1) from fibroblasts, resulting in significant suppression of the invasion ability of gastric cancer cells. Farnesyl anthranilate has been shown to reveal tumour growth-suppressive action in experimental murine melanomas models, as a probable consequence of down regulation of 3-hydroxy-3-methylglutaryl coenzyme A (HMG CoA) reductase activity. Antitumour activity of the anthranilamide CI-1040 has been demonstrated in preclinical models, particularly for pancreas, colon, and breast cancers. The CI-1040 activity has been correlated with its inhibition of mitogen-activated protein kinase (MAPk) cascade pathway. Moreover, the anthranilamide AAL993 has been described as a lead compound. (Cocco M T, Congiu C, Lilliu V Onnis V, Bioorg Med Chem Left, 2004, 23, 5787-5791, Cenzo Congiu, Maria Teresa Cocco, Lilliu V, Onnis V, J. Med. Chem. 2005, 48, 8245-8252).

However, the clinical efficacy for these anticancer agents is hindered by several limitations, such as poor water solubility, cardio toxicity, development of drug resistance and metabolic inactivation.

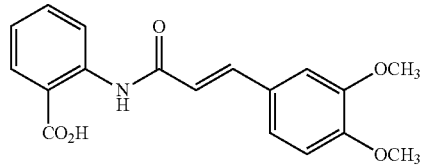

Tranilast

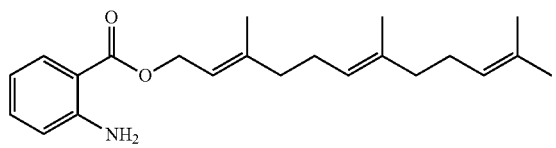

Farnesyl anthranilate

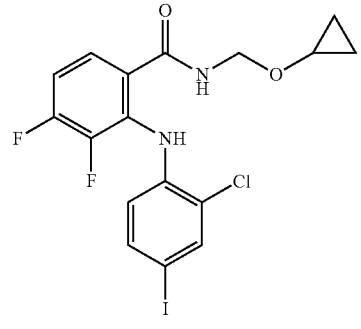

CI-1040

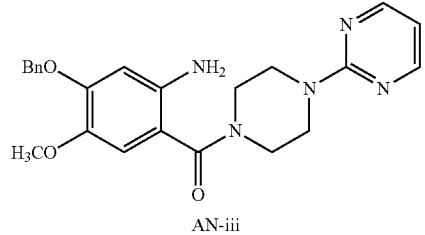

AN-iii

OBJECTIVES OF THE INVENTION

The main objective of the present invention is to provide novel anthranilic acid derivatives useful as antitumour agents.

Another object of the present invention is to provide a process for the preparation of novel anthranilic acid derivatives.

SUMMARY OF THE INVENTION

Accordingly the present invention provides novel anthranilic acid derivative of general formula 8, useful as potential anticancer agent:

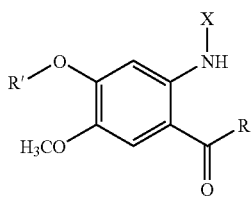

Formula 8 wherein R' is selected from alkyl-2-methoxyphenyl piperazine and benzyl;

R is selected from the group consisting of 2-methoxyphenyl piperazine, 2-pyridyl piperazine-1-yl, 2-pyrimidyl piperazine-1-yl, 4-quinazolinyl piperazine-1-yl, fluorenylamine, 4-[(2-{amino-5-(methoxy)-4-[(phenylmethyl)oxy]phenyl}carbonyl)hexahydro-1-pyrazinyl], and [(4 [2-amino-4-(benzyloxy)-5-methoxybenzoyl]aminophenyl)sulfonyl]-4-benzamine; and

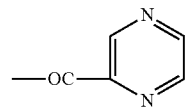

X is selected from H and

In an embodiment of the present invention the representative compounds of anthranilic acid derivative of formula 8 are as follows:
[2-amino-4-(benzyloxy)-5-methoxyphenyl][4-(2-methoxyphenyl)piperaz-ino]methanone (8a);
[2-amino-4-(benzyloxy)-5-methoxyphenyl][4-(2-pyridyl)piperazino]methanone (8b);
[2-amino-4-(benzyloxy)-5-methoxyphenyl][4-(2-pyrimidinyl)piperazino]methanone (8c);
[2-amino-4-(benzyloxy)-5-methoxyphenyl][4-(4-quinazolinyl)piperazino]methanone (8d);
N1-(9H-9-fluorenyl)-2-amino-4-(benzyloxy)-5-methoxybenzamide (8e);
(4-(benzyloxy)-5-methoxy-2-(pyrazine-2-carbamido)phenyl)(4-(2-methoxyphenyl)-piperazin-1-yl)methanone (8f);
{2-amino-5-(methyloxy)-4-[(phenylmethyl)oxy]phenyl}[4-({2-amino-5-(methyloxy)-4-[(phenylmethyl)oxy]phenyl}carbonyl)hexahydro-1-piperazinyl]methanone (8g);
N1-4-[(4[2-amino-4-(benzyloxy)-5-methoxybenzoyl]aminophenyl)sulfonyl]phenyl-2-amino-4-(benzyloxy)-5-methoxybenzamide (8h); and
(2-amino-5-methoxy4-3-[4-(2-methoxyphenyl)piperazino]propoxyphenyl)[4-(2-methoxyphenyl)piperazino]methanone (11).

In yet another embodiment the structural formula of the representative compounds of anthranilic acid derivative of general formula 8 are as follows:

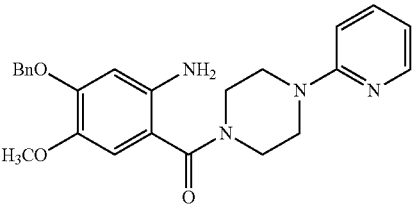

8a

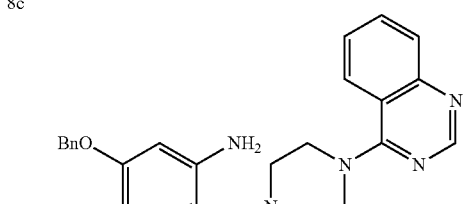

8b

8c

8e

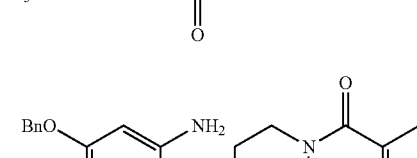

8f

11

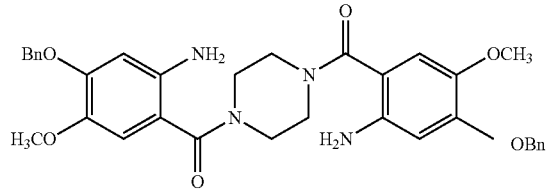

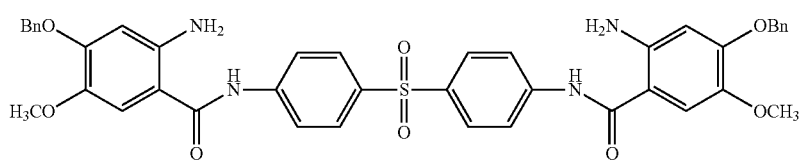

8h

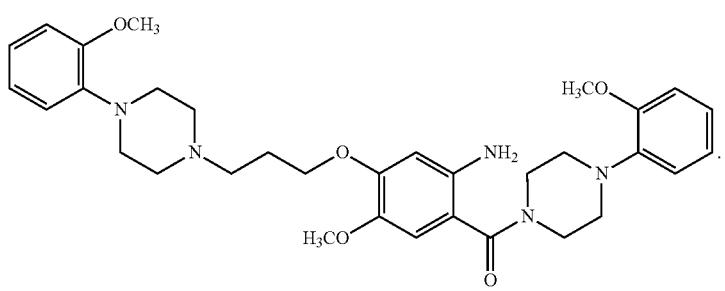

11

In yet another embodiment the novel anthranilic acid derivatives have the following characteristics:

Thermal denaturation data of Anthranilic acid with calf thymus (CT) DNA

| Compounds | [ANCD/DNA] molar ratio[b] | $\Delta T_m$ (°C.)[a] after incubation at 37°C. for | | |
|---|---|---|---|---|
| | | 0 h | 18 h | 36 h |
| 8a | 1:5 | 1.2 | 1.7 | 2.2 |
| 8b | 1:5 | 1.5 | 2.1 | 2.6 |
| 8c | 1:5 | 1.4 | 1.6 | 2.3 |
| 8d | 1:5 | 1.5 | 1.9 | 2.7 |
| 8e | 1:5 | 1.9 | 2.3 | 2.8 |
| 8f | 1:5 | 1.3 | 2.1 | 3.0 |
| 8g | 1:5 | 1.6 | 2.6 | 2.9 |
| 9a | 1:5 | 1.5 | 2.3 | 2.4 |
| 11 | 1:5 | 1.4 | 2.1 | 2.1 |
| DC-81 | 1:5 | 0.3 | 0.7 | |

[a]For CT-DNA alone at pH 7.00 ± 0.01, $T_m$ = 69.6° C. ± 0.01 (mean value from 10 separate determinations), all $\Delta T_m$ values are ±0.1-0.2° C.
[b]For a 1:5 molar ratio of [ligand]/[DNA], where CT-DNA concentration = 100 μM and ligand concentration = 20 μM in aqueous sodium phosphate buffer [10 mM sodium phosphate + 1 mM EDTA, pH 7.00 ± 0.01].
ANCD = Anthranilic acid derivative.

In yet another embodiment the novel anthranilic acid derivatives exhibits in vitro anticancer activity against human cell lines.

In yet another embodiment the human cancer lines used are derived from the cancer type selected from the group consisting of colon, leukemia, prostate, ovarian, oral, lung, cervix, CNS, melanoma and breast cancer.

In yet another embodiment the compounds 8a to 8e exhibits $\log_{10}$ GI50 (50% cell growth inhibition) mean graphs mid point against human tumour cell lines in the range of −5.0 to −7.0.

In yet another embodiment the compounds 8a to 8e exhibits $\log_{10}$ TGI (total cell growth inhibition) mean graphs mid point against human tumour cell lines in the range of −5.0 to −6.5.

In yet another embodiment the compounds 8a to 8e exhibits $\log_{10}$ LC50 (50% cell death) mean graphs mid point against human tumour cell lines in the range of −4.0 to −5.0.

In yet another embodiment the compounds 8a to 8e exhibits $\log_{10}$ GI50 (mol/L causing 50% growth inhibition) against human tumour cell lines in the range of −5.0 to −8.0.

The present invention further provides a process for the preparation of novel anthranilic acid derivative of general formula 8, useful as potential anticancer agent:

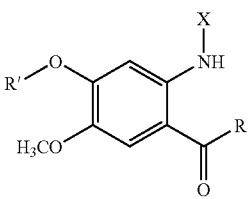

wherein R' is selected from alkyl-2-methoxyphenyl piperazine and benzyl;

R is selected from the group consisting of 2-methoxyphenyl piperazine, 2-pyridyl piperazine-1-yl, 2-pyrimidyl piperazine-1-yl, 4-quinazolinyl piperazine-1-yl, 9H-9-fluorenylamine, 4-[(2{amino-5-(methoxy)-4-[(phenylmethyl)oxy]phenyl}carbonyl)hexahydro-1-pyrazinyl], and [(4[2-amino-4-(benzyloxy)-5-methoxybenzoyl]aminophenyl)sulfonyl]-4-benzamine; and X is selected from H and

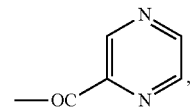

the said process comprising the steps of:
a) preparing the compound 4-benzoyloxy-5-methoxy-2-nitro benzoic acid of formula 6 from the compound of formula 1 by known method;

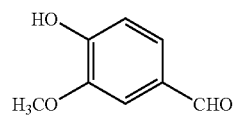

1

-continued

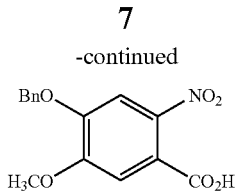

6 b) adding dimethylformamide (DMF) to a suspension of 4-benzyloxy-5-methoxy-2-nitro benzoic acid and thionyl chloride in dry benzene, under stirring, for a period of 5-7 hrs, followed by the evaporation of benzene, under vacuum, and redissolving the resultant oil in dry THF;

c) adding the above said resultant oil in dry THF obtained in step (b) to a suspension of triethyl amine and a reagent selected from the group consisting of 2-methoxy-phenyl piperazine, 2-pyridyl piperazine-1-yl, 2-pyrimidyl piperazine-1-yl, 4-quinazolinyl piperazine-1-yl, 9H-9-fluorenylamine, 4-[(4-aminophenyl)-sulfonyl]aniline and piperazine, over a period of 1-2 hrs, followed by the evaporation of THF, under vacuum, and washing the aqueous layer with ethyl acetate, adjusting the pH of the aqueous phase at 3 with HCl and extracting it with ethyl acetate, followed by washing with brine and drying to obtain the resultant compounds 7a-e and 7g-h;

d) reducing the above said compounds 7a-e obtained in step (c) with $SnCl_2$ in methanol, followed by evaporation of methanol under vacuum, and adjusting the pH of the aqueous layer at 8-8.5 with $NaHCO_3$ solution and extracting it with ethyl acetate, drying the combined organic phase, followed by evaporation, under vacuum, to obtain the desired corresponding anthranilic acid derivatives of formula 8a-e and 8g-h;

e) adding DMF to a suspension of pyrazine-2-carboxylic acid and thionyl chloride in dry benzene, under stirring, for 5-6 hrs, followed by the evaporation of benzene, dissolving the resultant oil in dry THF and adding it drop wise to a suspension of triethylamine and [2-amino-4-(benzyloxy)-5-methoxyphenyl][4-(2-methoxy-phenyl)piperazino] methanone (8a) obtained in step (d), evaporating THF after completion of the reaction and washing the aqueous layer with ethyl acetate and adjusting the pH at 3-3.5 with HCl, followed by extraction with ethyl acetate, washing and drying by known method, followed by evaporation to obtain the desired anthranilic acid derivative of formula 8f;

f) adding TFA to a suspension of [4-(benzyloxy)-5-methoxy-2-nitrophenyl][4-(2-methoxyphenyl)piperazino]methanone (7a) obtained in step (d), under stirring, and refluxing for a period of 7-9 hrs, followed by evaporation and adjusting the pH of the resultant oil at 8-8.5 with $NaHCO_3$ solution and extracting it with ethyl acetate, drying the combined organic phase, followed by evaporation, under vacuum, to obtain the compound [4-(hydroxyl-5-methoxy-2-nitrophenyl][4-(2-methoxyphenyl)piperazino]methanone of formula 8';

g) reacting the compound [4-(hydroxyl-5-methoxy-2-nitrophenyl][4-(2-methoxyphenyl)piperazino]methanone of formula 8' obtained in step (f) with 1,3-dibromo propane and $K_2CO_3$ in acetone, under stirring, for a period of 20-30 hrs, followed by evaporation of acetone, washing and extracting with ethyl acetate, followed by drying and evaporation to obtain the compound [4-(3-bromo propyloxy)-5-methoxy-2-nitrophenyl][4-(2-methoxyphenyl) piperazino]methano-ne (9);

h) reacting the compound [4-(3-bromo propyloxy)-5-methoxy-2-nitrophenyl][4-(2-methoxyphenyl)piperazino] methanone of formula 9 obtained in step (g) with 1-(2-methoxyphenyl)piperazine in acetone, under stirring, for 15-17 hrs, followed by evaporation of acetone, washing and extracting with ethyl acetate, followed by drying and evaporation to obtain the compound (5-methoxy-4-3-[4-(2-methoxyphenyl)piperazino]propoxy-2-nitrophenyl)[4-(2-methoxyphenyl)-piper-azino]methanone (10);

i) reducing the above said compound 10 obtained in step (h) with $SnCl_2$ in methanol, followed by evaporation of methanol, under vacuum, and adjusting the pH of the aqueous layer at 8-8.5 with $NaHCO_3$ solution and extracting it with ethyl acetate, drying the combined organic phase, followed by evaporation, under vacuum, to obtain the desired corresponding anthranilic acid derivative (11).

In yet another embodiment the compound 7 obtained in step (d) are as follows:
[4-(benzyloxy)-5-methoxy-2-nitrophenyl][4-(2-methoxyphenyl)piperazino]methanone (7a);
[4-(benzyloxy)-5-methoxy-2-nitrophenyl][4-(2-pyridyl)piperazino]methanone (7b);
[4-(benzyloxy)-5-methoxy-2-nitrophenyl][4-(2-pyrimidinyl)piperazino]methanone (7c);
[4-(benzyloxy)-5-methoxy-2-nitrophenyl][4-(4-quinazolinyl)piperazino]methanone (7d);
N1-(9H-9-fluorenyl)-4-(benzyloxy)-5-methoxy-2-nitrobenzamide (7e);
N1-4-[(4-[4-(benzyloxy)-5-methoxy-2-nitrobenzoyl]aminophenyl)sulfonyl]phenyl-4-(benzyloxy)-5-methoxy-2-nitrobenzamide (7g);
{5-(methyloxy)-2-nitro-4-[(phenylmethyl)oxy]phenyl}[4-({5-(methyloxy)-2-nitro-4-[(phenylmethyl)oxy]phenyl}carbonyl)hexahydro-1-pyrazinyl]methanone (7h).

In yet another embodiment the representative compounds of anthranilic acid derivative of formula 8 are as follows:
[2-amino-4-(benzyloxy)-5-methoxyphenyl][4-(2-methoxyphenyl)piperazino]methanone (8a);
[2-amino-4-(benzyloxy)-5-methoxyphenyl][4-(2-pyridyl)piperazino]methanone (8b);
[2-amino-4-(benzyloxy)-5-methoxyphenyl][4-(2-pyrimidinyl)piperazino]-methanone (8c);
[2-amino-4-(benzyloxy)-5-methoxyphenyl][4-(4-quinazolinyl)piperazino]methanone (8d);
N1-(9H-9-fluorenyl)-2-amino-4-(benzyloxy)-5-methoxybenzamide (8e)
(4-(benzyloxy)-5-methoxy-2-(pyrazine-2-carbamido)phenyl)(4-(2-methoxyphenyl)piperazin-1-yl)-methanone (8f);
{2-amino-5-(methyloxy)-4[(phenylmethyl)oxy]phenyl}[4-({2-amino-5-(methylo-xy)-4-[(phenylmethyl)oxy]phenyl}carbonyl)hexahydro-1-piperazinyl]methanone (8g);
N1-4-[(4-[2-amino-4-(benzyloxy)-5-methoxybenzoyl]aminophenyl)sulfonyl]phenyl-2-amino-4-(benzyloxy)-5-methoxybenzamide (8h);
(2-amino-5-methoxy-4-3-[4-(2-methoxyphenyl)piperazino] propoxyphenyl)[4-(2-methoxyphenyl)piperazino]methanone (11).

DETAIL DESCRIPTION OF THE INVENTION

These new analogues of anthranilic acid hybrids linked at secondary amine position have shown promising DNA binding activity and efficient anticancer activity in various cell lines. The molecules synthesized are of immense biological significance with potential sequence selective DNA-binding property. This resulted in design and synthesis of new congeners as illustrated in Scheme-1, which comprise:
1. The ether linkage at C-8 position of anthranilic acid intermediates with [2-(n-bromoalkyl)-5-chlorophenyl](phenyl)methanone moiety.
2. The amide linkage at acid position of anthranilic acid intermediates.
3. Refluxing the reaction mixtures for 16 h.
4. Synthesis of novel anthranilic acid hybrids anticancer agents.
5. Purification by column chromatography using different solvents like ethyl acetate, hexane, dichloromethane and methanol.

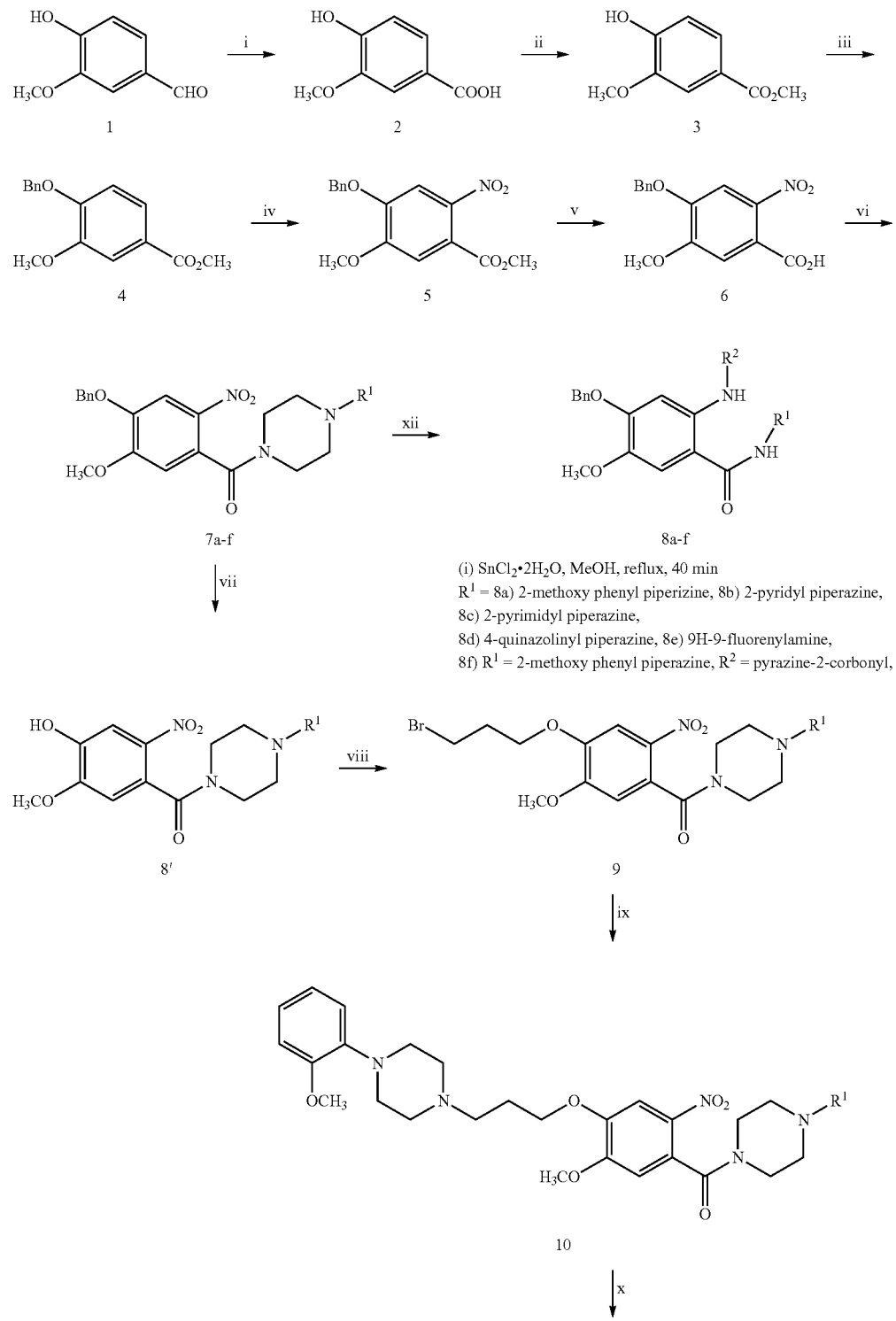

Scheme 1

(i) SnCl$_2$·2H$_2$O, MeOH, reflux, 40 min
R$^1$ = 8a) 2-methoxy phenyl piperizine, 8b) 2-pyridyl piperazine,
8c) 2-pyrimidyl piperazine,
8d) 4-quinazolinyl piperazine, 8e) 9H-9-fluorenylamine,
8f) R$^1$ = 2-methoxy phenyl piperazine, R$^2$ = pyrazine-2-corbonyl, -continued

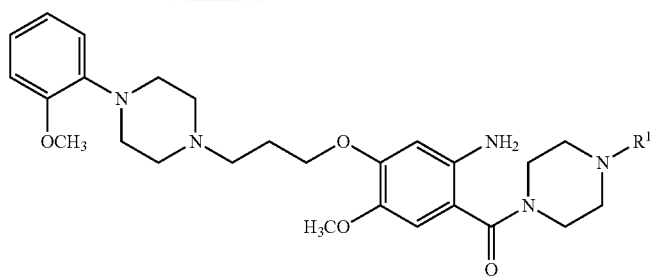

11

R¹ = 2-methoxyphenyl

Reagents and conditions: a) NH₂SO₃H, ClO₂, H₂O
b) Ph CH₂ Br, K₂CO₃, CH₃COCH₃, reflux, 16 h, 82%
c) SnCl₄ — HNO₃, CH₂Cl₂, -25 °C., 5 min, 88%
d) 1M LiOH, THF, MeOH, H₂O (3:1:1), rt, 12 h, 90%
e) SOCl₂, L-proline methyester hydrochloride, Et3N H₂O, 0 °C., 3 h 80%
f) DIBAL-H, CH₂Cl2, -78 °C., 45 min, 65%
g) EtSH — TMSCl, CH₂Cl₂, rt, 16 h, 85%
h) N-methyl piperazine, K₂CO₃, CH₃CN, reflux, 48 h, 70%
i) SnCl₂·2H₂O, MeOH, reflux, 40 min, 75%
j) HgCl₂ — CaCO₃, CH₃CN: H₂O (4:1), 8-12 h, 52%.

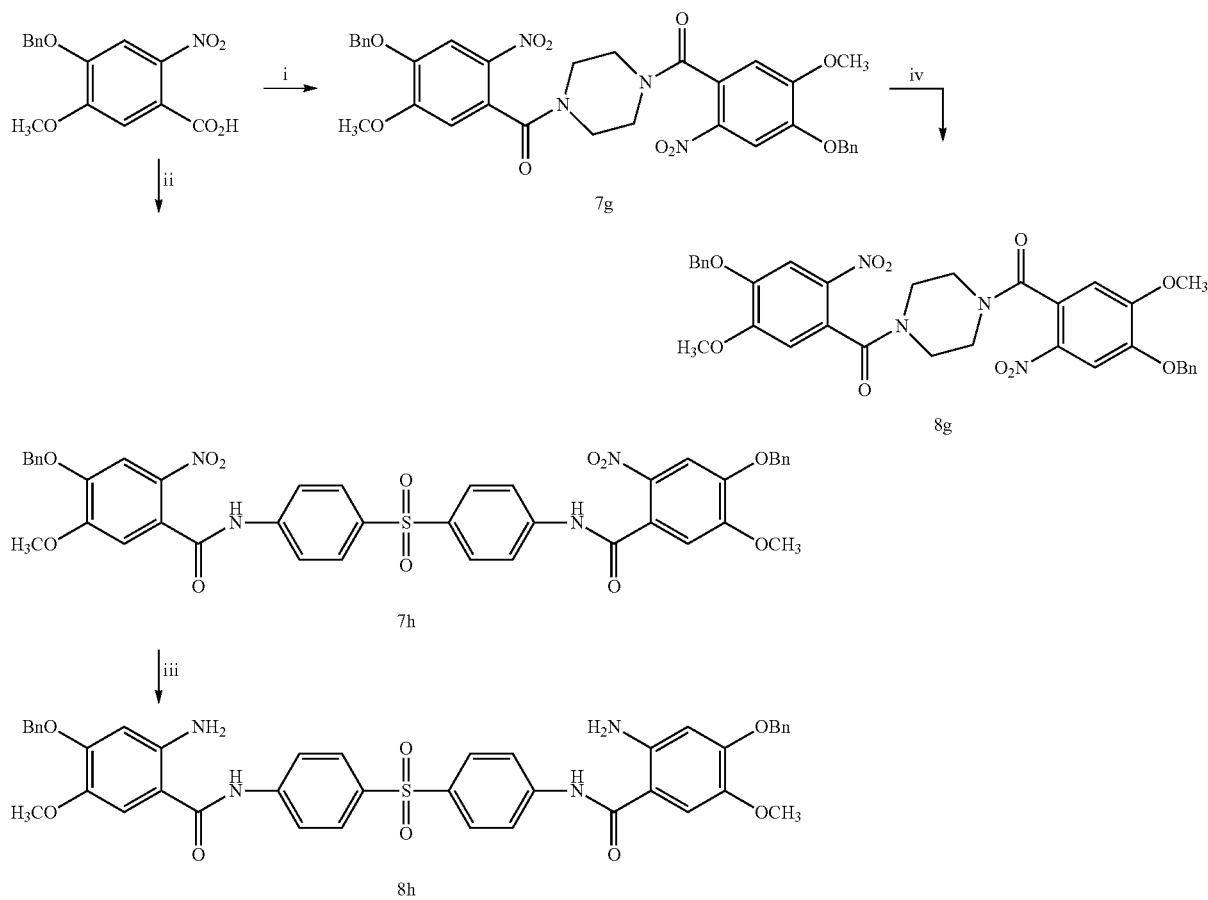

(i) piperazine.THF, rt; (ii) 4-[(4-aminophenyl)sulfonyl]aniline, THF, rt;
(iii) SnCl₂·2H₂O, MeOH, Reflux; (iv) SnCl₂·2H₂O, MeOH, Reflux.

The following examples are given by way of illustration and therefore should not be construed to the present limit of the scope of invention.

Example 1

[4-(Benzyloxy)-5-methoxy-2-nitrophenyl][442-methoxyphenyl)piperazino]-methanone (7a)

DMF was added to a stirred suspension of 4-benzoyloxy-5-methoxy-2-nitro benzoic acid (6) (0.500 mg, 1.65 mmol) and thionyl chloride (3 ml) in dry benzene (30 ml) and the stirring was continued for 6 h. The benzene was evaporated in vacuum and the resultant oil dissolved in dry THF (50 ml) and added drop wise over a period of 1 h to a stirred suspension of 1-(2-methoxyphenyl)piperazine (316 mg 15.6 mmol) triethyl amine (5 ml). After the completion of addition, the reaction mixture was brought to ambient temperature and stirred for an additional hour. The THF was evaporated in vacuum and the aqueous layer was washed with ethyl acetate. The aqueous phase was then adjusted to pH 3 using 6 N HCl and extracted with ethyl acetate and washed with brine, dried over $Na_2SO_4$ and evaporated in vacuum to afford the crude product of 2-amino-4-benzyloxy)-5-methoxyphenyl][4-(2-methoxyphenyl)piperazino]methanone (7a) in 93% yield (670 mg, 85% yield). $^1$H NMR (CDCl$_3$) δ 3.20-3.30 (m, 4H), 3.40-3.55 (m, 4H), 3.85 (S, 3H), 3.95 (s, 3H), 5.20 (s, 2H), 6.80-7.00 (m, 5H), 7.30-7.50 (m, 5H), 7.70 (s, 1H); FABMS: 477 (M+H)$^+$.

Example 2

[2-Amino-4-(benzyloxy)-5-methoxyphenyl][4-(2-methoxyphenyl)piper-azino]methanone (8a)

[4-(Benzyloxy)-5-methoxy-2-nitrophenyl][4-(2-methoxyphenyl)piperazino]methanone (7a) (500 mg, 1.04 mmol) was dissolved in methanol (10 mL), SnCl$_2$.2H$_2$O (706 mg, 3.14 mmol) was added and refluxed until the TLC indicated the completion of the reaction. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude. This was further purified by column chromatography using ethyl acetate:hexane (6:4) as a solvent system to obtain the pure product (8a) (425 mg, 91% yield). $^1$H NMR (CDCl$_3$) δ 3.20-3.30 (m, 4H), 3.45-3.55 (m, 4H), 3.85 (s, 3H), 3.98 (s, 3H), 5.20 (s, 2H), 6.19 (s, broad NH$_2$) 6.80-7.00 (m, 5H), 7.30-7.50 (m, 5H), 7.70 (s, 1H); FABMS: 447 (M+H)$^+$.

Example 3

[4-(Benzyloxy)-5-methoxy-2-nitrophenyl][4-(2-pyridyl)piperazino]-methanone (7b)

DMF was added to a stirred suspension of 4-benzoyloxy-5-methoxy-2-nitro benzoic acid
6) (0.500 mg, 1.65 mmol) and thionyl chloride (3 ml) in dry benzene (30 ml) and the stirring was continued for 6 h. The benzene was evaporated in vacuum and the resultant oil dissolved in dry THF (50 ml) and added dropwise over a period of 1 h to a stirred suspension of (2-pyridyl)piperazine (268 mg 1.65 mmol) triethyl amine (5 ml). After the completion of addition, the reaction mixture was brought to ambient temperature and stirred for an additional hour. The THF was evaporated in vacuum and the aqueous layer was washed with ethyl acetate. The aqueous phase was then adjusted to pH 3 using 6 N HCl and extracted with ethyl acetate and washed with brine, dried over Na$_2$SO$_4$ and evaporated in vacuum to afford the crude product [4-(benzyloxy)-5-methoxy-2-nitrophenyl][4-(2-pyridyl)piperazino]methanone (7b) (610 mg, in 82% yield). $^1$H NMR (CDCl$_3$) δ 3.10-3.25 (m, 4H), 3.65-3.80 (m, 4H), 3.95 (s, 3H), 5.20 (s, 2H), 7.00-7.50 (m, 5H), 7.70 (s, 1H), 8.25-8.35 (d, J=9.05, 2H); FABMS: 448 (M+H)$^+$.

Example 4

[2-Amino-4-(benzyloxy)-5-methoxyphenyl][4-(2-pyridyl)piperazino]-methanone (8b)

[4-(Benzyloxy)-5-methoxy-2-nitrophenyl][4-(2-pyridyl)piperazino]methanone (7b) (500 mg, 1.11 mmol) was dissolved in methanol (10 mL), SnCl$_2$.2H$_2$O (753 mg, 3.3 mmol) was added and refluxed until the TLC indicated the completion of the reaction. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude (450 mg, 95% yield), This was further purified by column chromatography using ethyl acetate:hexane (6:4) as a solvent system to obtain the pure product 8b (650 mg, in 94% yield). $^1$H NMR (CDCl$_3$) δ 3.15-3.30 (m, 4H), 3.70-3.80 (m, 4H), 3.95 (s, 3H), 5.20 (s, 2H), 6.20 (s, br,) 7.00-7.50 (m, 5H), 7.70 (s, 1H), 8.25-8.35 (d, J=9.05, 2H); FABMS: 418 (M+H)$^+$.

Example 5

[4-(Benzyloxy)-5-methoxy-2-nitrophenyl][4-(2-pyrimidinyl)piperazino]-methanone (7c)

DMF was added to a stirred suspension of 4-benzoyloxy-5-methoxy-2-nitro benzoic acid (6) (0.500 mg, 1.65 mmol) and thionyl chloride (3 ml) in dry benzene (30 ml) and the stirring was continued for 6 h. The benzene was evaporated in vacuum and the resultant oil dissolved in dry THF (50 ml) and added dropwise over a period of 1 h to a stirred suspension of 1-(2-pyrimidinylpyperazine)piperazine (270 mg 1.65 mmol) triethyl amine (5 ml). After the completion of addition, the reaction mixture was brought to ambient temperature and stirred for an additional hour. The THF was evaporated in vacuum and the aqueous layer was washed with ethyl acetate. The aqueous phase was then adjusted to pH 3 using 6 N HCl and extracted with ethyl acetate and washed with brine, dried over Na$_2$SO$_4$ and evaporated in vacuum to afford the crude product of (7c), (635 mg, in 85% yield). $^1$H NMR (CDCl$_3$) δ 3.10-3.25 (m, 4H), 3.60-3.80 (m, 4H), 3.95 (s, 3H), 5.20 (s, 2H), 6.55-6.55, (t, 1H) 6.75 (s, 1H), 7.30-7.60 (m, 5H), 7.80 (s, 1H); FABMS: 449 (M+H)$^+$.

Example 6

[2-Amino-4-(benzyloxy)-5-methoxyphenyl][4-(2-pyrimidinyl)piperazino]-methanone (8c)

[4-(Benzyloxy)-5-methoxy-2-nitrophenyl][4-(2-pyrimidinyl)piperazino-]methanone (7c) (500 mg, 1.11 mmol) was dissolved in methanol (10 mL), SnCl$_2$.2H$_2$O (751 mg, 3.3 mmol) was added and refluxed until the TLC indicated the completion of the reaction. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude This was further purified by column chromatography using ethyl acetate:hexane (6:4) as a solvent system to obtain the pure product (8c) (420 mg, 90% yield). $^1$H NMR (CDCl$_3$) δ 3.10-3.25 (m, 4H), 3.60-3.80 (m, 4H), 3.95 (s, 3H), 5.20 (s, 2H), 6.20 (s, br), 6.45-6.55 (t, 1H) 6.75 (s, 1H), 7.30-7.55 (m, 5H), 7.80 (s, 1H); FABMS: 419 (M+H)$^+$.

Example 7

[4-(Benzyloxy)-5-methoxy-2-nitrophenyl][4-(4-quinazolinyl)piperazino]-methanone (7d)

DMF was added to a stirred suspension of 4-benzoyloxy-5-methoxy-2-nitro benzoic acid (6) (0:500 mg, 1.65 mmol) and thionyl chloride (3 ml) in dry benzene (30 ml) and the stirring was continued for 6 h. The benzene was evaporated in vacuum and the resultant oil dissolved in dry THF (50 ml) and added dropwise over a period of 1 h to a stirred suspension of (4-quinazolinyl)piperazine (350 mg, 1.65 mmol) triethyl amine (5 ml). After the completion of addition, the reaction mixture was brought to ambient temperature and stirred for an additional hour. The THF was evaporated in vacuum and the aqueous layer was washed with ethyl acetate. The aqueous phase was then adjusted to pH 3 using 6 N HCl and extracted with ethyl acetate and washed with brine, dried over Na$_2$SO$_4$ and evaporated in vacuum to afford the crude product of (7d), (700 mg in 84% yield). $^1$H NMR (CDCl$_3$) δ 3.15-3.30 (m, 4H), 3.65-3.75 (m, 4H), 3.95 (s, 3H), 5.20 (s, 2H), 6.45-6.55 (t, 1H) 6.70 (s, 1H), 7.30-7.50 (m, 5H), 7.55-7.65 (t, 1H), 7.65 (s, 1H), 7.70-7.90 (m, 2H), 7.85-7.95 (m, 2H); FABMS: 500 (M+H)$^+$.

Example 8

[2-Amino-4-(benzyloxy)-5-methoxyphenyl][4-(4-quinazolinyl)piperazino]-methanone (8d)

[4-(Benzyloxy)-5-methoxy-2-nitrophenyl][4-(4-quinazolinyl)piperazino]methanone (600 mg, 1.2 mmol) was dissolved in methanol (10 mL), SnCl$_2$.2H$_2$O (810 mg, 3.6 mmol) was added and refluxed until the TLC indicated the completion of the reaction. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude (450 mg, 95% yield). This was further purified by column chromatography using ethyl acetate:hexane (6:4) as a solvent system to obtain the pure product (8d) (672 mg, 80% yield). $^1$H NMR (CDCl$_3$) δ 3.20-3.30 (m, 4H), 3.65-3.75 (m, 4H), 3.95 (s, 3H), 5.20 (s, 2H), 6.20 (s, broad NH$_2$), 6.45-6.55, (t, 1H) 6.70 (s, 1H), 7.30-7.50 (m, 5H), 7.55-7.65 (t, 1H), 7.65 (s, 1H), 7.70-7.90, (m, 2H), 7.85-7.95, (m, 2H); FABMS: 470 (M+H)$^+$.

Example 9

N1-(9H-9-Fluorenyl)-4-(benzyloxy)-5-methoxy-2-nitrobenzamide (7e)

DMF was added to a stirred suspension of 4-benzoyloxy-5-methoxy-2-nitro benzoic acid (6) (0.500 mg, 1.65 mmol) and thionyl chloride (3 ml) in dry benzene (30 ml) and the stirring was continued for 6 h. The benzene was evaporated in vacuum and the resultant oil dissolved in dry THF (50 ml) and added dropwise over a period of 1 h to a stirred suspension of 9H-9-fluorenamine (326, 15.6 mmol) triethylamine (5 ml). After the completion of addition, the reaction mixture was brought to ambient temperature and stirred for an additional hour. The THF was evaporated in vacuum and the aqueous layer was washed with ethyl acetate. The aqueous phase was then adjusted to pH 3 using 6 N HCl and extracted with ethyl acetate and washed with brine, dried over Na$_2$SO$_4$ and evaporated in vacuum to afford the crude product of (7e) (620 mg in 80% yield). $^1$H NMR (CDCl$_3$) δ 3.95 (s, 3H), 5.20 (s, 2H), 5.70 (s, 1H), 6.70 (s, 1H), 7.00-7.41 (m, 5H), 7.45-7.706 (m, 9H); FABMS: 466 (M+H)$^+$.

Example 10

N1-(9H-9-Fluorenyl)-2-amino-4-(benzyloxy)-5-methoxybenzamide (8e)

N1-(9H-9-fluorenyl)-4-(benzyloxy)-5-methoxy-2-nitrobenzamide of formula (7e) (500 mg, 1.07 mmol) was dissolved in methanol (10 mL), SnCl$_2$.2H$_2$O (839 mg, 3.2 mmol) was added and refluxed until the TLC indicated the completion of the reaction. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude N1-(9H-9-fluorenyl)-2-amino-4-(benzyloxy)-5-methoxybenzamide (450 mg, 95% yield). This was further purified by column chromatography using ethyl acetate:hexane (6:4) as a solvent system to obtain the pure product (8e) (610 mg, 84% yield). $^1$H NMR (CDCl$_3$) δ 3.95 (s, 3H), 5.20 (s, 2H), 5.70 (s, 1H), 6.70 (s, 1H), 7.00-7.41 (m, 5H), 7.45-7.706 (m, 9H); FABMS: 436 (M+H)$^+$.

Example 11

N1-4-[(4-[4-(Benzyloxy)-5-methoxy-2-nitrobenzoyl]aminophenyl)-sulfonyl]phenyl-4-(benzyloxy)-5-methoxy-2-nitrobenzamide (7h)

DMF was added to a-stirred suspension of 4-benzoyloxy-5-methoxy-2-nitro benzoic acid (6) (500 mg, 1.65 mmol) and thionyl chloride (5 mL) in dry benzene (30 mL) and the stirring was continued for 6 h. The benzene was evaporated in vacuum and the resultant oil dissolved in dry THF (50 mL) and added drop wise over a period of 1 h to a stirred suspension of 4-[(4-aminophenyl)sulfonyl]aniline (326 mg, 15.6 mmol) triethylamine (5 mL). After the completion of addition, the reaction mixture was brought to ambient temperature and stirred for an additional hour. The THF was evaporated in vacuum and the aqueous layer was washed with ethyl acetate. The aqueous phase was then adjusted to pH 3 using 6 N HCl and extracted with ethyl acetate and washed with brine, dried over Na$_2$SO$_4$ and evaporated in vacuum to afford the crude product of 7 h (830 mg in 84% yield). $^1$H NMR (CDCl$_3$): δ 5.20 (s, 4H), 6.85 (s, 1H), 7.20-7.90 (m, 12H), 8.05-8.25 (m, 10H); FABMS: 818 (M+H)$^+$.

Example 12

N1-4-[(4-[2-Amino-4-(benzyloxy)-5-methoxybenzoyl]aminophenyl)-sulfonyl]phenyl-2-amino-4-(benzyloxy)-5-methoxybenzamide (8h)

N1-4-[(4-[4-(benzyloxy)-5-methoxy-2-nitrobenzoyl]aminophenyl)sulfonyl]phenyl-4-(benzyloxy)-5-methoxy-2-nitrobenzamide of formula 7h (500 mg, 1.27 mmol) was dissolved in methanol (10 mL), SnCl$_2$.2H$_2$O (943 mg, 3.2 mmol) was added and refluxed until the TLC indicated the completion of the reaction. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude N1-4-[(4-[2-amino-4-(benzyloxy)-5-methoxybenzoyl]amino-phenyl)sulfonyl]phenyl-2-amino-4-(benzyloxy)-5-methoxybenzamide (650 mg, 95% yield). This was further purified by column chromatography using ethyl acetate:hexane (6:4) as a solvent system to obtain the pure product 8 h (425 mg, 84% yield). $^1$H NMR (CDCl$_3$): δ 5.22 (s, 4H), 6.88 (s, 1H), 7.21-7.94 (m, 12H), 8.10-8.30 (m, 10H); FABMS: 758 (M+H)$^+$.

Example 13

[4-(Hydroxy-5-methoxy-2-nitrophenyl][4-(2-methoxyphenyl)piperazino]-methanone (8')

Trifluoroacetic acid (TFA) was added to a stirred suspension of [4-(benzyloxy)-5-methoxy-2-nitrophenyl][4-(2-methoxyphenyl)piperazino]methanone (7a) (500 mg, 1.65 mmol) the stirring with refluxed has continued for 8 h. The TFA was evaporated in vacuum and the oil residue was then adjusted to pH 8 with 10% NaHCO$_3$ solution and extracted with ethyl acetate (2×30 mL). The combined organic phase was dried over Na$_2$SO$_4$ and evaporated under vacuum to afford the crude [4-(hydroxy-5-methoxy-2-nitrophenyl][4-(2-methoxyphenyl)piperazino]-methanone. This was further purified by column chromatography using ethyl acetate:hexane (6:4) as a solvent system to obtain the pure product 8' (410 mg, 82% yield). $^1$H NMR (CDCl$_3$): δ 3.20-3.30 (m, 4H), 3.40-3.55 (m, 4H), 3.85 (s, 3H), 3.95 (s, 3H), 5.20 (s, 2H), 6.85 (s, 1H), 7.30-7.50 (m, 4H), 7.70 (s, 1H); FABMS: 309 (M+H)$^+$.

Example 14

[4(3-Bromopropyloxy)-5-methoxy-2-nitrophenyl][4-(2-methoxyphenyl)-piperazino]methanone (9)

To a stirred suspension of [4-(hydroxy-5-methoxy-2-nitrophenyl][4-(2-methoxy-phenyl)piperazino]methanone (8') (500 mg, 1.65 mmol), 1,3-dibromo propane (316 mg 15.6 mmol) and K$_2$CO$_3$ (816 mg 26.6 mmol) in acetone (30 mL) and the stirring was continued for 24 h. The acetone was evaporated in vacuum and the aqueous layer was washed with ethyl acetate and extracted with ethyl acetate and washed with brine, dried over Na$_2$SO$_4$ and evaporated in vacuum to afford the crude product to [4-(3-bromo propyloxy)-5-methoxy-2-nitrophenyl][4-(2-methoxyphenyl)piperazino]methanone (9) in 93% yield (630 mg, 85% yield). $^1$H NMR (CDCl$_3$): δ 1.60-2.15 (m, 2H), 2.98-3.12 (t, 2H, J=7.31 Hz), 3.20-3.30 (m, 6H), 3.40-3.55 (m, 4H), 3.85 (s, 3H), 3.95 (s, 3H), 5.20 (s, 2H), 6.85 (s, 1H), 7.30-7.50 (m, 4H), 7.70 (s, 1H); FABMS: 431 (M+H)$^+$.

Example 15

(5-Methoxy-4-3-[4-(2-methoxyphenyl)piperazino]propoxy-2-nitrophenyl)-[4-(2-methoxyphenyl)piperazino]methanone (10)

To a stirred suspension of [4-(3-bromopropyloxy)-5-methoxy-2-nitrophenyl][4-(2-methoxyphenyl)piperazino]methanone (9) (500 mg, 1.65 mmol), 1-(2-methoxyphenyl)piperazine (316 mg 15.6 mmol) and K$_2$CO$_3$ (816 mg 26.6 mmol) in acetone (30 mL) and the stirring was continued for 16 h. The acetone was evaporated in vacuum and the aqueous layer was washed with ethyl acetate and extracted with ethyl acetate and washed with brine, dried over Na$_2$SO$_4$ and evaporated in vacuum to afford the crude product to (5-methoxy-4-3-[4-(2-methoxyphenyl)-piperazino]propoxy-2-nitrophenyl)[4-(2-methoxyphenyl)piperazino]methanone (10) in 93% yield (670 mg, 85% yield). $^1$H NMR (CDCl$_3$): δ 1.60-2.15 (m, 2H), 2.98-3.12 (t, 2H, J=7.31 Hz), 3.18-3.36 (m, 8H), 3.38-3.60 (m, 10H), 3.85 (m, 3H), 3.95 (s, 3H), 4.00-4.15 (m, 3H) 6.85-7.00 (m, 8H), 7.20-7.40 (m, 1H), 7.70-7.80 (d, 1H, J=6.81 Hz); FABMS: 619 (M+H)$^+$.

Example 16

(2-Amino-5-methoxy-4-3-[4-(2-methoxyphenyl)piperazino]propoxy-phenyl)[4-(2-methoxyphenyl)piperazino]methanone (11)

(5-Methoxy-4-3-[4-(2-methoxyphenyl)piperazino]propoxy-2-nitrophenyl)[4-(2-methoxy phenyl)piperazino]methanone of formula (10) (500 mg, 1.07 mmol) was dissolved in methanol (10 mL), SnCl$_2$.2H$_2$O (839 mg, 3.2 mmol) was added and refluxed until the TLC indicated the completion of the reaction. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude N1-(9H-9-fluorenyl)-2-amino-4-(benzyloxy)-5-methoxybenzamide (450 mg, 95% yield). This was further purified by column chromatography using ethyl acetate:hexane (6:4) as a solvent system to obtain the pure product (11) (610 mg, 84% yield). $^1$H NMR (CDCl$_3$): δ 2.10-2.80 (m, 4H), 2.98-3.18 (m, 8H), 3.38-3.60 (m, 10H), 3.85-3.95-4.05 (m, 6H), 6.78-7.45 (m, 9H), 7.70-7.80 (m, 1H); FABMS: 589 (M+H)$^+$.

Example 17

(4-(Benzyloxy)-5-methoxy-2-(pyrazine-2-carbamido)phenyl)(4-(2-methoxyphenyl)piperazin-1-yl)methanone (8f)

DMF was added to a stirred suspension of pyrazine-2-carboxylic acid (248 mg, 2.0 mmol) and thionyl chloride (5 mL) in dry benzene (30 mL) and the stirring was continued for 6 h. The benzene was evaporated in vacuum and the resultant oil dissolved in dry THF (50 mL) and added drop wise over a period of 1 h to a stirred suspension of [2-amino-4-(benzyloxy)-5-methoxyphenyl][4-(2-methoxyphenyl)piperazino]methanone (8a) (457 mg, 1.0 mmol) and triethylamine (5 mL). After the completion of addition, the reaction mixture was brought to ambient temperature and stirred for an additional hour. The THF was evaporated in vacuum and the aqueous layer was washed with ethyl acetate. The aqueous phase was then adjusted to pH 3 using 6 N HCl and extracted with ethyl acetate and washed with brine, dried over Na$_2$SO$_4$ and evaporated in vacuum to afford the crude product of (80 (400 mg, 71% yield). $^1$H NMR (CDCl$_3$) δ 3.21-3.32 (m, 4H), 3.46-3.55 (m, 4H), 3.86 (s, 3H), 3.97 (s, 3H), 5.22 (s, 2H), 6.80-7.03 (m, 5H), 7.32-7.52 (m, 5H), 7.59-7.65 (m, 2H), 7.71 (s, 1H), 7.83 (s, 1H); FABMS: 553 (M+H)$^+$.

Example—18

{5-(Methyloxy)-2-nitro-4-[(phenylmethyl)oxy]phenyl}[4-({5-(methyloxy)-2-nitro-4-[(phenylmethyl)oxy]phenyl}carbonyl)-1-piperazinyl]methanone (7g)

DMF was added to a stirred suspension of 4-benzoyloxy-5-methoxy-2-nitro benzoic acid (6) (1.8 gm, 6.0 mmol) and thionyl chloride (10 ml) in dry benzene (50 ml) and the stirring was continued for 6 h. The benzene was evaporated in vacuum and the resultant oil dissolved in dry THF (50 ml) and added drop wise over a period of 1 h to a stirred suspension of piperazine (172 mg 2.0 mmol) and triethyl amine (6 ml). After the completion of addition, the reaction mixture was brought to ambient temperature and stirred for an additional hour. The THF was evaporated in vacuum and the aqueous layer was washed with ethyl acetate. The aqueous phase was then adjusted to pH 3 using 6 N HCl and extracted with ethyl acetate and washed with brine, dried over $Na_2SO_4$ and evaporated in vacuum to afford the crude product of {5-(methyloxy)-2-nitro-4-[(phenylmethyl)oxy]phenyl}[4-({5-(methyloxy)-2-nitro-4-[(phenylmethyl)oxy]phenyl}-carbonyl)hexahydro-1-pyrazinyl]methanone (7g) in (650 mg, 50% yield). $^1$H NMR (CDCl$_3$) 3.22-3.34 (m, 4H), 3.43-3.56 (m, 4H), 3.86 (s, 6H), 5.21 (s, 4H), 6.81-7.11 (m, 12H), 7.71 (s, 2H); FABMS: 656 (M+H)$^+$.

Example—19

{2-Amino-5-(methyloxy)-4[(phenylmethyl)oxy]phenyl}[4-({2-amino-5-(methyloxy)-4-[(phenylmethyl)oxy]phenyl}carbonyl)hexahydro-1-pyrazinyl]methanone (8g)

{5-(methyloxy)-2-nitro-4-[(phenylmethyl)oxy]phenyl}[4-({5-(methyloxy)-2-nitro-4-[(phenylmethyl)oxy]phenyl}carbonyl)hexahydro-1-pyrazinyl]methanone of formula (7g) (400 mg, 0.6 mmol) was dissolved in methanol (10 mL), SnCl$_2$.2H$_2$O (685 mg, 3.0 mmol) was added and refluxed until the TLC indicated the completion of the reaction. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude product 8g {5-(methyloxy)-2-nitro-4-[(phenylmethyl)oxy]phenyl}[4-({5-(methyloxy)-2-nitro-4-[(phenylmethyl)oxy]phenyl}-carbonyl)hexahydro-1-pyrazinyl]methanone. This was purified by column chromatography using ethyl acetate:hexane (6:4) as a solvent system to obtain the pure product (8g) (180 mg, 50% yield). $^1$H NMR (CDCl$_3$) δ 3.22-3.36 (m, 4H), 3.42-3.55 (m, 4H), 3.85 (s, 6H), 5.23 (s, 4H), 6.25 (s, broad 2H) 6.81-7.11 (m, 12H), 7.71 (s, 2H); FABMS: 596 (M+H)$^+$.

Thermal Denaturation Studies

Compounds were subjected to thermal denaturation studies with duplex-form calf thymus DNA (CT-DNA) using an adaptation of a reported procedure. Working solutions in aqueous buffer (10 mM NaH$_2$PO$_4$/Na$_2$HPO$_4$, 1 mM Na$_2$EDTA, pH 7.00+/−0.01) containing CT-DNA (100 μM in phosphate) and the PBD (20 μM) were prepared by addition of concentrated ANCD solutions in DMSO to obtain a fixed [ANCD]/[DNA] molar ratio of 1:5. The DNA-ANCD solutions were incubated at 37° C. for 0, 18, and 36 h prior to analysis. Samples were monitored at 260 nm using a Beckman DU-7400 spectrophotometer fitted with high performance temperature controller, and heating was applied at 1° C. min$^{-1}$ in the 40-90° C. range. DNA helix coil transition temperatures (Tm) were obtained from the maxima in the (dA260)/dT derivative plots. Results are given as the mean+/−standard deviation from three determinations and are corrected for the effects of DMSO co-solvent using a linear correction term. Drug-induced alterations in DNA melting behaviour are given by: ΔTm=Tm (DNA+ANCD)− Tm (DNA alone), where the Tm value for the ANCD-free CT-DNA is 69.0+/−0.01. The fixed [ANCD]/[DNA] ratio used did not result in binding saturation of the host DNA duplex for any compound examined. Compound 8a, 8b, 8c, 8d, 8e, 8f, 8g, 8h and 11 at 0 hr, 18 hr and 36 hr gradually increased at 37° C.

TABLE 1

Thermal denaturation data of Anthanilic acid with calf thymus (CT) DNA

| Compounds | [ANCD/DNA] molar ratio$^b$ | $\Delta T_m$ (° C.)$^a$ after incubation at 37° C. for | | |
|---|---|---|---|---|
| | | 0 h | 18 h | 36 h |
| 8a | 1:5 | 1.2 | 1.7 | 2.2 |
| 8b | 1:5 | 1.5 | 2.1 | 2.6 |
| 8c | 1:5 | 1.4 | 1.6 | 2.3 |
| 8d | 1:5 | 1.5 | 1.9 | 2.7 |
| 8e | 1:5 | 1.9 | 2.3 | 2.8 |
| 8f | 1:5 | 1.3 | 2.1 | 3.0 |
| 8g | 1:5 | 1.6 | 2.6 | 2.9 |
| 8h | 1:5 | 1.5 | 2.3 | 2.4 |
| 11 | 1:5 | 1.4 | 2.1 | 2.1 |
| DC-81 | 1:5 | 0.3 | 0.7 | |

$^a$For CT-DNA alone at pH 7.00 ± 0.01, $T_m$ = 69.6° C. ± 0.01 (mean value from 10 separate determinations), all $\Delta T_m$ values are ±0.1-0.2° C.
$^b$For a 1:5 molar ratio of [ligand]/[DNA], where CT-DNA concentration = 100 μM and ligand concentration = 20 μM in aqueous sodium phosphate buffer [10 mM sodium phosphate + 1 mM EDTA, pH 7.00 ± 0.01].
$^c$ANCD = Anthranilic acid derivative Biological Activity: some of compounds down in vitro biological activity studies were carried out at the National Cancer Institute, Maryland, USA.

In vitro evaluation of cytotoxic activity: Compounds were evaluated for in vitro anticancer activity against sixty human tumour cells derived from nine cancer types (colon, prostate, oral, lung, cervix and breast cancer) as shown in (Table 1, 2 and 3) 8b, 8c, 8d, and 8e, were evaluated for in vitro anticancer activity against sixty human tumour cells derived from nine cancer types (leukemia, non-small-cell lung, colon, CNS, melanoma, ovarian, prostate, and breast cancer) as shown in (Table 2 and 3). For the compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of log$_{10}$ TGI and log$_{10}$ LC50 as well as log$_{10}$ GI50 for 8a, 8b, 8c, 8d, and 8e, are listed in (Table 2 and 3). As demonstrated by mean graph pattern, compound 8b, 8c, 8d, and 8e exhibited an interesting profile of activity and selectivity for various cell lines. The mean graph mid point of log$_{10}$ TGI and log$_{10}$ LC50 showed similar pattern to the log$_{10}$ GI50 mean graph mid points.

TABLE 2

Log$_{10}$GI50 log$_{10}$TGI and log$_{10}$LC50 mean graphs midpoints (MG_MID) of in vitro cytotoxicity data for the representative compounds against human tumour cell lines

| Compound | Log$_{10}$GI50 | Log$_{10}$TGI50 | Log$_{10}$LC50 |
|---|---|---|---|
| 8a | −5.47 | −5.24 | −4.19 |
| 8b | −5.62 | −5.12 | −4.05 |
| 8c | −5.47 | −5.47 | −4.47 |
| 8d | −5.62 | −5.62 | −4.62 |
| 8e | −6.47 | −6.06 | −4.19 |

TABLE 3

Log GI50 (concentration in mol/L causing 50% growth inhibition) values for anthranilic acid hybrids

| Cancer | Compound (8a) | Compound (8b) | Compound (8c) | Compound (8d) | Compound (8e) |
|---|---|---|---|---|---|
| Leukemia | −5.26 | −5.26 | −5.26 | −5.39 | −5.37 |
| Nonsmall-cell-lung | −5.44 | −5.34 | −5.14 | −5.87 | −5.86 |
| Colon | −5.07 | −5.17 | −5.47 | −5.29 | −5.77 |
| CNS | −5.23 | −5.23 | −5.23 | −5.75 | −5.26 |
| Melanoma | −5.35 | −5.75 | −5.75 | −5.14 | −5.75 |
| Ovarian | −5.24 | −5.24 | −5.24 | −4.93 | −5.00 |
| Renal | −5.25 | −5.25 | −5.25 | −5.26 | −4.82 |
| Prostate | −5.18 | −4.78 | −4.78 | −5.14 | −6.45 |
| Breast | −5.47 | −5.17 | −5.17 | −5.15 | −8.00 |

Each cancer type represents the average of six to nine different cancer cell lines. The compounds 8a, 8b, 8c, 8d, 8e and 8f were evaluated for in vitro anticancer activity against sixty human tumour cells derived from nine cancer types (leukemia, colon, prostate, renal melanoma CNS, lung, cervix and breast cancer) as shown in Table 3. Compounds 8b, 8c, 8d and 8e show promising cytotoxicity against some cancer cell lines (Table 2). Compounds 8b, 8c, 8d and 8e have been evaluated for their in vitro cytotoxicity in selected human cancer cell lines of colon (Colo205), lung (Hop-62), cervix (SiHa), prostate (DU145, PC3), oral (DWD, HT1080), and breast (MCF7, Zr-75-1) origin. A protocol of 48 h continuous drug exposure has been used and an Adriamycin (ADR) protein assay has been used to estimate cell viability or growth. The results are expressed as percent of cell growth determined relative to that of untreated control cells. Among them 8a, 8d and 8e, exhibits a wide spectrum of activity against sixty cell lines in nine cell panels, with $GI_{50}$ value of <20 nM. In the non-small cell lung cancer panel, the growth of EKVX, NCI-H226 cell lines leukemia cell cancer panel the growth of HL-60 (TB) were affected by compound 8b with $GI_{50}$ values as 12.4, 13.6 and 16.5 nM respectively. In the breast cancer panel, the growth of BT-549, MCF-7 cell lines are 10.3, and 17.6. In the prostate cancer panel, the growth of DU-145, PC-3 cell lines are 11.3, and 19.2. The $GI_{50}$ values of compound In the CNS cancer panel, the growth of SF-539, SNB-75 cell lines are 12.3, 14.6 and 17.5. The $GI_{50}$ values of compound 8d against colon cancer COLO 205, HCT-116 and KM12 cell lines are 11.2, 16.3 and 14.6 nM respectively. The GI50 values for compound 8d against CNS SF-295, SF-539, SNB-19 and SNB-75 cell lines are in a range of 11.8-24.2 nM. Two cancer cell lines (MCF-7, T47D) in the breast cancer cell panel were affected by compound 8d with $GI_{50}$ values of 12.6, 13.2, nM respectively. In this study compound 8d exhibited cytotoxicity activity against renal and prostate cancer panels with $GI_{50}$ values (1.16-32.4 nM), compound 8b exhibits activity against fifty-five cell lines in nine cancer cell panels with $GI_{50}$ values of <10 mM. Compound 8e exhibits activity against fifty-seven cell lines in nine cancer cell panels, $GI_{50}$ values of <10 mM. In vitro cytotoxicity of compounds 8a, and 8b in selected cancer cell lines has been illustrated in Table 3. The average $GI_{50}$ values for each cancer panel of compounds 8b, 8c, 8d and 8e have been illustrated in above Table 2 and 3

We claim:

1. A compound of formula 8:

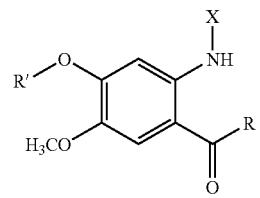

Formula 8 wherein:

R' is benzyl;

R is selected from the group consisting of 2-methoxy phenyl piperazine, 2-pyridyl piperazine-1-yl, 2-pyrimidyl piperazine-1-yl, 4-quinazolinyl piperazine-1-yl, and 4-[(2-{amino-5-(methoxy)-4-{phenylmethyl)-oxy}-phenyl}carbonyl)hexadydro-1-pyrazinyl]; and X is H.

2. The compound of formula 8 according to claim 1, selected from the group consisting of:

[2-amino-4-(benzyloxy)-5-methoxyphenyl][4-(2-methoxyphenyl)piperazino]methanone;

[2-amino-4-(benzyloxy)-5-methoxyphenyl][4-(2-pyridyl)piperazino]methanone;

[2-amino-4-(benzyloxy)-5-methoxyphenyl][4-(2-pyrimidinyl)-piperazino]methanone;

[2-amino-4-(benzyloxy)-5-methoxyphenyl][4-(4-quinazolinyl)-piperazino]methanone; and

[2-amino-5-(methyloxy)-4[(phenyl-methyl)oxy]phenyl}[4-({2-amino-5-(methyloxy)-4-[(phenyl-methyl)oxy]phenyl}-carbonyl)hexahydro-1-piperazinyl]-methanone.

3. A method of suppressing proliferation of human cancer cell lines, wherein the human cancer cell lines are selected from the group consisting of colon, leukemia, prostate, ovarian, renal, non-small lung, central nervous system, melanoma, and breast, comprising administering a compound of formula 8 to a subject in need thereof,

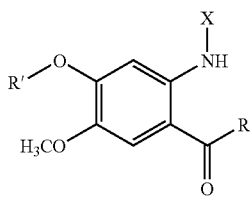

Formula 8 wherein:
R' is benzyl;
R is selected from the group consisting of 2-methoxy phenyl piperazine, 2-pyridyl piperazine-1-yl, 2-pyrimidyl piperazine-1-yl, 4-quinazolinyl piperazine-1-yl, and 4-[(2-{amino-5-(methoxy)-4-{phenylmethyl)-oxy}-phenyl}carbonyl)hexadydro-1-pyrazinyl]; and
X is H.

4. The method of claim 3, wherein the compound of formula 8 exhibits $\log_{10}$GI50 (50% cell growth inhibition) mean graphs mid point against human tumor cell lines in the range of −5.47 to −5.62.

5. The method of claim 3, wherein the compound of formula 8 exhibits $\log_{10}$TGI (total cell growth inhibition) mean graphs mid point against human tumor cell lines in the range of −5.12 to −5.62.

6. The method of claim 3, wherein the compound of formula 8 exhibits $\log_{10}$LC50 (50% cell death) mean graphs mid point against human tumor cell lines in the range of −4.05 to −4.62.

7. The method of claim 3, wherein the compound of formula 8 exhibits $\log_{10}$ GI50 (mol/L causing 50% growth inhibition) against human tumor cell lines in the range of −4.78 to −5.87.

8. A process for preparing the compound of claim 1 of structural formula 8, comprising:

a) adding dimethylformamide (DMF) to a suspension of 4-benzyloxy-5-methoxy-2-nitrobenzoic acid and thionyl chloride in dry benzene, under stirring, for a period of 5-7 hours, followed by evaporation of the benzene, under vacuum, and redissolving a resultant oil in dry tethrahydrofuran (THF);

b) adding the oil in dry THF obtained in (a) to a suspension of triethylamine and a reagent selected from the group consisting of 2-methoxyphenylpiperazine, 2-pyridylpiperazine, 2-pyrimidylpiperazine, 4-quinazolinylpiperazine, and piperazine, over a period of 1-2 hours to form a desired product, followed by the evaporation of THF, under vacuum, and washing a resulting aqueous layer with ethyl acetate, adjusting the aqueous phase to pH 3 with hydrochloric acid and extracting the aqueous layer with ethyl acetate, followed by washing with brine and drying to obtain an intermediate compound; and c) reducing the intermediate obtained in (b) with $SnCl_2$ in methanol, followed by evaporation of methanol, under vacuum, and adjusting an aqueous layer to pH 8-8.5 with $NaHCO_3$ solution and extracting the aqueous layer with ethyl acetate, drying the combined organic phase, followed by evaporation under vacuum.

9. The process of claim 8, wherein the intermediate structure is selected from the group consisting of (4-(benzyloxy)-5-methoxy-2-nitrophenyl)(4-(2-methoxyphenyl) piperazin-1-yl)methanone, (4-(benzyloxy)-5-methoxy-2-nitrophenyl)(4-(pyridin-2-yl)piperazin-1-yl)methanone, (4-(benzyloxy)-5-methoxy-2-nitrophenyl) (4-(pyrimidin-2-yl)piperazin-1-yl)methanone, (4-(benzyloxy)-5-methoxy-2-nitrophenyl)(4-(quinazolin-4-yl) piperazin-1-yl)methanone, and piperazine-1,4-diylbis((4-(benzyloxy)-5-methoxy-2-nitrophenyl)methanone).

\* \* \* \* \*